(12) United States Patent
Tang et al.

(10) Patent No.: US 6,701,181 B2
(45) Date of Patent: Mar. 2, 2004

(54) MULTI-PATH OPTICAL CATHETER

(75) Inventors: Jing Tang, Allston, MA (US); Guillermo J. Tearney, Cambridge, MA (US); Brett E. Bouma, Quincy, MA (US); S. Eric Ryan, Hopkinton, MA (US); Simon Furnish, Louisville, KY (US); Andres Zuluaga, Boston, MA (US)

(73) Assignee: InfraReDx, Inc., Cambridge, MA (US)

( * ) Notice: Subject to any disclaimer, the term of this patent is extended or adjusted under 35 U.S.C. 154(b) by 0 days.

(21) Appl. No.: 09/871,770

(22) Filed: May 31, 2001

(65) Prior Publication Data

US 2002/0183623 A1 Dec. 5, 2002

(51) Int. Cl.⁷ .................................. A61B 6/00
(52) U.S. Cl. ............... 600/478; 600/476; 385/115; 385/117; 385/119; 606/13; 606/15; 606/16; 606/17
(58) Field of Search ............... 600/476, 478, 600/407, 34; 385/33, 34, 60, 73, 74, 115, 119; 606/13, 14, 15–18; 604/96.01

(56) References Cited

U.S. PATENT DOCUMENTS

| | | | |
|---|---|---|---|
| 3,856,000 A | 12/1974 | Chikama | 128/6 |
| 4,040,413 A | 8/1977 | Ohshiro | 128/6 |
| 4,224,929 A | 9/1980 | Furihata | 128/5 |
| 4,620,769 A | 11/1986 | Tsuno | 350/96.26 |
| 4,697,577 A | 10/1987 | Forkner | 128/6 |
| 4,832,473 A | 5/1989 | Ueda | 350/506 |
| 5,106,387 A | 4/1992 | Kittrell et al. | 606/15 |
| 5,179,934 A | 1/1993 | Nagayoshi et al. | 128/4 |
| 5,197,470 A * | 3/1993 | Helfer et al. | 600/342 |
| 5,380,317 A * | 1/1995 | Everett et al. | 606/15 |
| 5,649,924 A * | 7/1997 | Everett et al. | 606/15 |
| 5,953,477 A * | 9/1999 | Wach et al. | 385/115 |
| 6,416,234 B1 * | 7/2002 | Wach et al. | 385/70 |
| 6,423,055 B1 * | 7/2002 | Farr et al. | 606/15 |
| 6,564,088 B1 | 5/2003 | Soller et al. | |

* cited by examiner

Primary Examiner—Marvin M. Lateef
Assistant Examiner—Jeoyuh Lin
(74) Attorney, Agent, or Firm—Fish & Richardson P.C.

(57) ABSTRACT

First and second optical-redirectors mounted on a catheter couple radiation to a target along separate first and second paths. Either the first or second optical-redirectors, or both, can include a steering mechanism for selecting the first and/or second path.

30 Claims, 18 Drawing Sheets

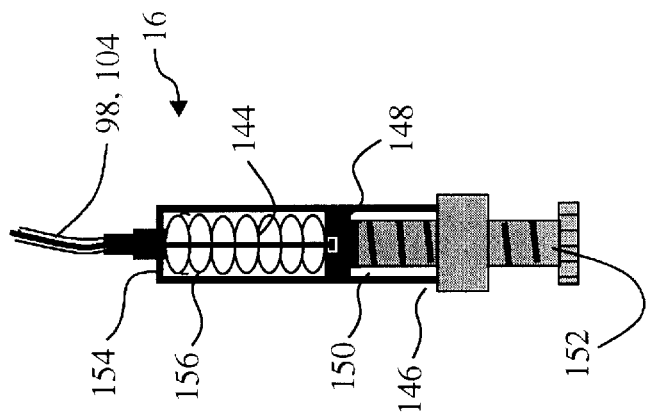
FIG. 20
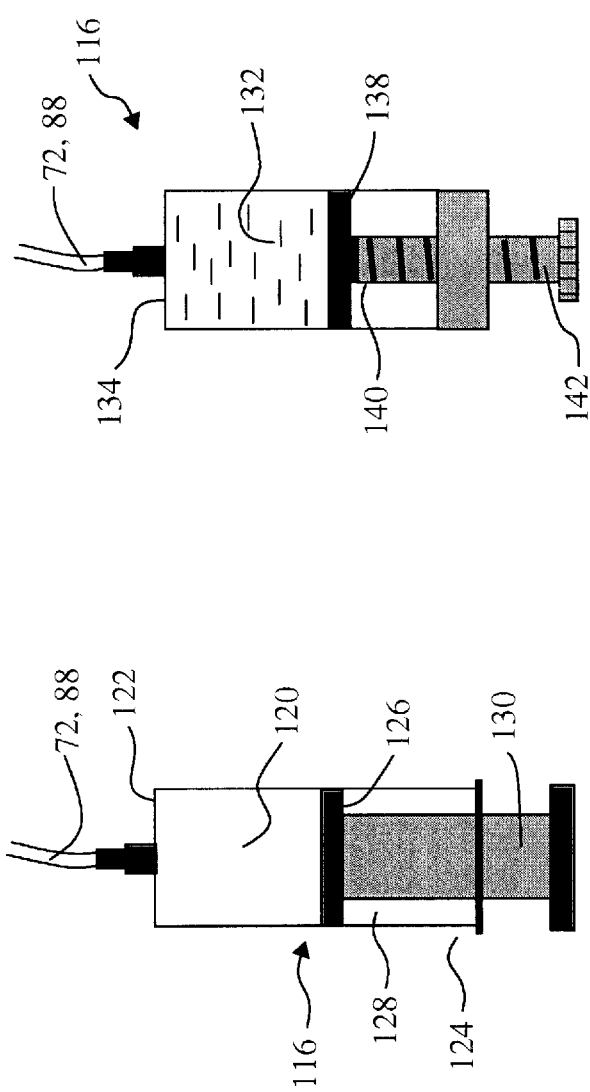
FIG. 19
FIG. 18

MULTI-PATH OPTICAL CATHETER

FIELD OF INVENTION

The invention relates to photo-medical devices, and more particularly, to photo-medical devices that use radiation to detect structures.

BACKGROUND

Heart attacks are a major cause of death, disability, and health-care expense in the U.S. and other industrialized societies. Convincing new clinical data demonstrates that the rupture of non-occlusive, vulnerable plaques causes the majority of heart attacks. It has become increasingly evident that although hard plaque may produce severe obstruction in the coronary arteries, it is often the less prominent, asymptomatic soft vulnerable plaques that are prone to rupture.

The majority of vulnerable plaques are pools of lipid covered by a thin fibrous cap. The rupture of a vulnerable plaque releases this stored lipid into the blood. This initiates a chemical chain reaction that often culminates in the formation of a large blood clot in the coronary artery. The blood clot deprives the heart muscle of blood, and hence oxygen. The eventual result of this oxygen deprivation is a heart attack.

Because the lipid pool of a vulnerable plaque is covered, it cannot easily be seen by visible light. In addition, because the lipid pool tends to grow radially outward into the blood vessel, it does not significantly constrict blood flow. As a result, it is not readily detectable in an angiogram.

Ultrasonic waves have been used to detect vulnerable plaques. However, the level of detail, or resolution, is generally insufficient for accurate diagnosis. In addition, bombardment of the thin fibrous cap by sound waves can potentially trigger a rupture.

Magnetic resonance imaging (MRI) has also been used to detect vulnerable plaques. However, MRI requires long exposure times and are therefore not suitable for detecting moving structures. As a result, attempts to detect plaques in moving structures, such as coronary arteries, often result in blurred images.

Infrared light is known to penetrate short distances into the vascular wall and can therefore be used to detect such plaques as well as other subendothelial pathology. A difficulty associated with use of infrared radiation to detect vulnerable plaques is that a significant fraction of the incident infrared radiation is reflected from the inner wall. Only a small portion of this incident infrared radiation penetrates into the inner wall. Of this small portion, a still smaller portion emerges again from behind the inner wall. This portion must be separated from the infrared radiation reflected from the wall.

SUMMARY

The invention is based on the recognition that when attempting to observe a structure that lies on another side of an interface between two media, it is often advantageous to illuminate the structure from one direction while simultaneously observing it from another direction. This enables one to observe the structure without the glare of specular reflection of radiation from the illumination source.

The underlying physical principle of the invention, will be apparent to anyone who has attempted to observe an object underwater on a dark night. If one were to shine a flashlight into the water and stand directly above the flashlight, all one would see would be the reflection of the flashlight from the waters surface. Any light returning from the object of interest would be overwhelmed by the brilliance of the glare. In contrast, if one were instead to look into the water along a different path than that followed by the beam of the light, one would be able to observe underwater objects illuminated by the flashlight, essentially by side-stepping this glare. However, if the path were too different, for example if one were observing from a point inches above the water surface, one would no longer be able to see underwater. This suggests the existence of an optimal path for observing underwater structures (i.e., structures on the other side of a boundary between two media).

In one embodiment, the invention includes first and second optical-redirectors mounted on a catheter. The first optical-redirector couples radiation between itself and a target along a first path. The second optical-redirector couples radiation between itself and the target along a second path. Either the first or second optical-redirectors, or both, can include a steering mechanism for selecting the first and/or second path.

In another embodiment, the invention provides a conduit having a longitudinal axis extending between a proximal portion and a distal portion. First and second waveguides extend between the proximal portion of the conduit and the distal portion of the conduit. These waveguides guide radiation longitudinally along the conduit. First and second optical-redirectors are in communication with the first and second waveguides respectively. These optical-redirectors are oriented to direct radiation along first and second paths extending between the first and second waveguides and a target.

In one aspect of the invention, the first optical-redirector comprises a conical surface having a cone axis parallel to the longitudinal axis of the conduit, the conical surface having a flare angle relative to the cone axis. The conical surface comprises a truncated half-cone or a truncated cone.

Various other optical-redirector designs are within the scope of the invention. For example, the first optical-redirector can re-direct radiation either by reflection or by refraction. The first optical-redirector can also be integrated into the first waveguide. This can be achieved, for example, by providing the first waveguide with a distal face having a surface normal vector with a radial component. Radiation traveling along the first waveguide can then reflect off the distal end and proceed sideways, or radially, out of the waveguide and onto the target. Conversely, radiation from the target can enter the waveguide, reflect off the distal end, and travel down the waveguide.

The first and second optical-redirectors can be on two discrete structures. Alternatively, the first and second optical-redirectors can be integrated into a single structure. For example, a single reflecting structure may have two facets, one of which is coupled to the first waveguide and the other one of which is coupled to the second waveguide.

Either the first or second optical-redirectors, or both, can include a steering mechanism, such as an actuator coupled to the optical-redirector. Where the optical-redirector includes a conical surface, the actuator can be configured to change the flare angle of the conical surface. Alternatively, the actuator can be configured to translate the optical-redirector along the longitudinal axis.

An actuator for changing the flare angle of a conical surface can be an inflatable balloon coupled to the conical surface. In this case, a change in volume of the balloon controls the flare angle of the conical surface. The actuator can also be a translating member coupled to the conical surface so that translation of the translating member controls the flare angle.

The first path can also be controlled by changing the position of the first and/or second optical-redirector along the longitudinal axis. In this aspect of the invention, the actuator includes a control wire coupled to the conical surface for translating the conical surface along the longitudinal axis.

One type of conical surface whose flare angle can be changed is made up of several reflecting panels. Each reflecting panel has a base end, and a free end longer than the base end. Each reflecting panel is pivotable about the base end between a closed position and an open position. Adjacent reflecting panels can overlap such that when each reflecting panel is pivoted to its open position, the plurality of reflecting panels forms a continuous reflecting surface.

Control of the first and second paths can be manual or automatic. In an embodiment in which automatic control of the first and second paths is available, a feedback loop can move the first optical-redirector relative to the second optical-redirector on the basis of a signal received from at least one of the first optical-redirector or the second optical-redirector. Such a feedback loop can include a detector in communication with the second waveguide, a motor in communication with the first actuator, and a processor in communication with the detector and with the motor. The processor is configured to drive the motor in response to a signal received from the detector.

Another aspect of the invention includes directing illuminating radiation along a first path extending between the catheter and the target, and collecting re-entrant radiation from the target along a second path extending between the target and the catheter. Reentrant radiation received from the target can then be analyzed to detect a structure on or in the target. In one aspect of the invention, the first and/or second paths are selected to enhance recovery of the re-entrant radiation.

As used herein, the term optical-redirector is used to describe a structure that couples radiation between a guiding structure and free space. The term waveguide refers to any such guiding structure. A conduit refers to any structure for providing a mechanical framework for mounting the various other elements of the invention so that they can be delivered to a target. The conduit includes catheters, endoscopes, and similar instruments.

Unless otherwise defined, all other technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE FIGURES

FIGS. 18–20 are schematic diagrams of representative actuators used in the system of FIG. 17.

DETAILED DESCRIPTION

An apparatus incorporating the invention directs radiation toward a target, such as an inner wall of a blood vessel, along a first path. A portion of this radiation, referred to as "penetrating radiation," passes through the inner wall and interacts with structures, herein referred to as subendothelial structures, between the inner wall and the outer wall. These interactions include absorption and scattering by those structures.

A portion of the penetrating radiation passes back out through the inner wall and reenters the lumen. This portion, referred to as the re-entrant radiation, carries information regarding the subendothelial structures with which it has interacted. A pre-requisite to recovering this information is to recover the re-entrant radiation.

To avoid recovering primarily specular reflection from the inner wall of the blood vessel, an optical-redirector, such as a reflector, is oriented to intercept re-entrant radiation propagating along a second path. The second path is selected to be different enough from the first path to avoid receiving specular reflections, but close enough to receive re-entrant radiation having sufficient power to rise above the ambient noise level. The optimal difference between the first and second paths depends on a variety of factors, some of which can change with time and with location within a blood vessel. Hence, the apparatus preferably provides for independent adjustment of the first and/or second paths. The first and second paths can differ because they intersect different points on the target, i.e. different regions of the inner wall. Alternatively, the first and second paths can differ because they intersect the same point on the target but at different angles.

Figure 1:
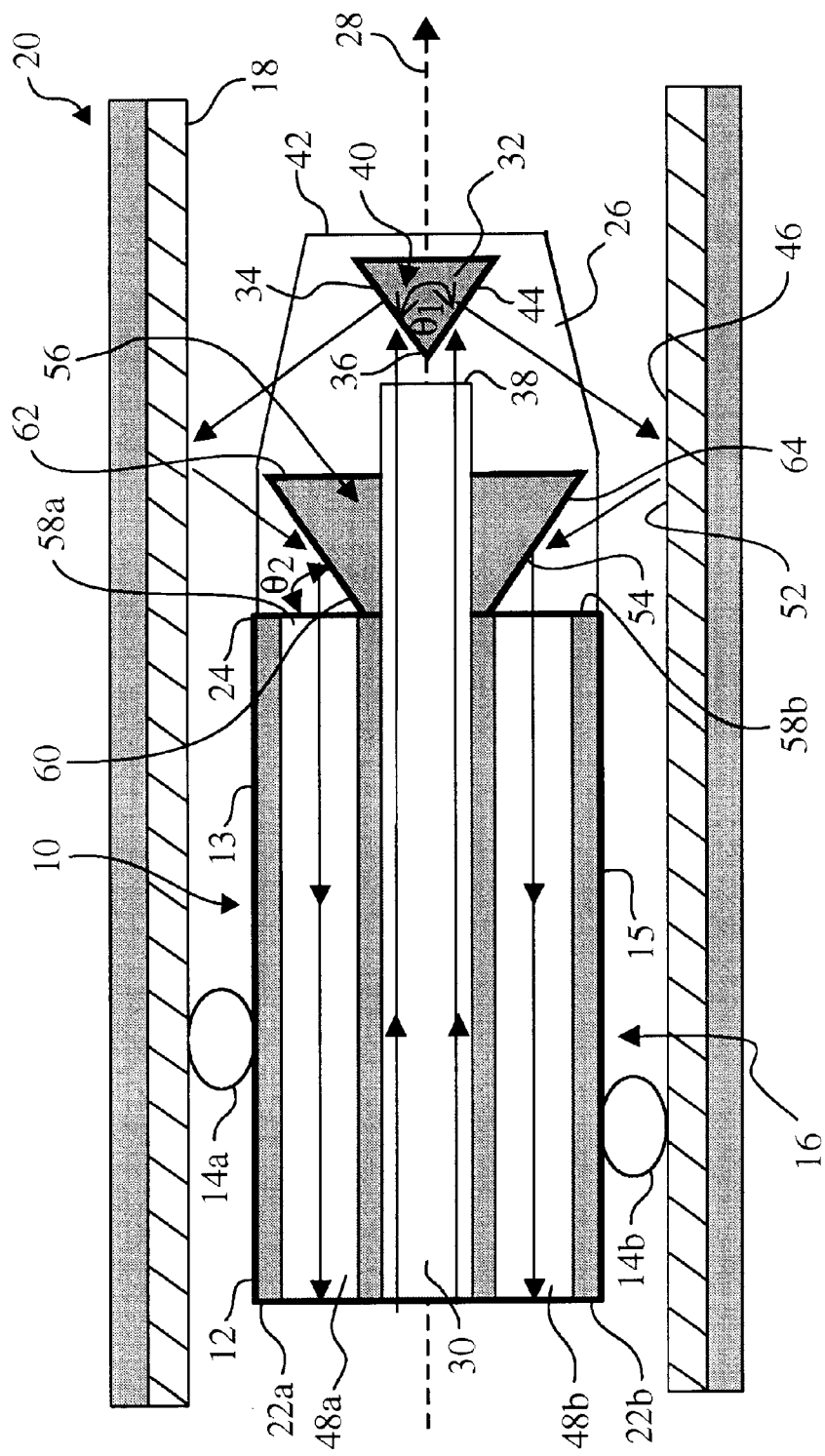
FIG. 1 is a longitudinal cross-section of a catheter having reflectors with fixed flare angles and fixed locations.

FIG. 1 shows a distal portion 10 of a catheter 12 that incorporates the invention. First and second positioning balloons 14a–b center the distal portion 10 of the catheter 12 in a lumen 16 defined by an inner wall 18 of a blood vessel 20. These positioning balloons 14a–b are coupled to a control fluid source (not shown) by first and second control fluid lumens 22a–b extending longitudinally along the periphery of the catheter 12. It will be appreciated that additional positioning balloons may be present but not shown in the cross-section of FIG. 1.

The catheter 12 has a typical diameter of 1–15 mm and a typical length of 500–3500 mm. A sheath 13 covering the distal portion 10 of the catheter 12 protects the various optical structures therein. To ensure flexibility over most of the catheters length, the sheath 13 preferably extends only over the distal portion 10 of the catheter 12. However, in some embodiments, the sheath 13 can extend the length of the catheter 12. The sheath 13 is made of a flexible material such as vinyl, polychloride, polytetrafluoroethylene ("PTFE"), polyethylene, or a similar material that is opaque to radiation at the frequency to be used.

A protective enclosure 15 outside the sheath 13 facilitates insertion of the catheter 12 into a human or animal blood vessel or body cavity. The protective enclosure 15 is made of a biocompatible material such as polyethylene.

The catheter 12 can be inserted into a patient through a through an endoscope, a thoracoscope, or a laparoscope. The catheter 12 can be inserted through a percutaneous puncture, or through a naturally occurring orifice such as the mouth, the nostril, the anus, the urethra, and the vagina.

The catheter 12 has a distal tip 24 on which is mounted a housing 26 that is transparent at those frequencies used for illuminating the inner wall 18 of the blood vessel 20. As shown in the figures, the housing 26 is a frusto-conical structure. However, the housing 26 can be another shape such as hemispherical, lenticular, flat, or any other shape. A bonding agent or wrapping material can be used to secure the joint between the catheter 12 and the housing 26.

Suitable materials for the housing 26 include fused silica, glass, sapphire, or a polymer such as polyethylene, PTFE, FEP, polyurethane, or nylon. The selection of material depends in part on the ability of that material to transmit radiation at those wavelength(s) to be used for detection of tissue. Such wavelengths are typically in the infrared range (from the near-infrared to the far-infrared). However, in some applications, the wavelengths can also be in the ultraviolet range or in the visible range.

Extending along a longitudinal axis 28 of the catheter 12 is an illumination fiber 30 that carries radiation from an emitter (not shown), coupled to the proximal end of the catheter 12, to a first optical redirector, which in this case includes an illuminating reflector 32, mounted in a distal chamber 34 of the housing 26. The distal chamber 34 is a chamber having transparent walls, typically made of the same material as the housing. To avoid Fresnel reflections, the walls of the distal chamber 34 are coated with an anti-reflective coating. The illuminating reflector 32 is a conical structure having a narrow end 36 facing an output face 38 of the illumination fiber 30 and a flared end 40 facing a distal wall 42 of the housing 26.

In operation, radiation traveling on the illumination fiber 30 exits the output face 38 of the fiber 30 and impinges on a proximal surface 44 of the illuminating reflector 32. The radiation reflects from the proximal surface 44 and illuminates a first annular region 46 of the inner wall 18. The location of the first annular region 46 is determined by a flare angle of the illuminating reflector 32.

Extending parallel to the longitudinal axis 28 of the catheter 12 are one or more collection fibers 48a–b that carry re-entrant radiation from the distal tip 24 of the catheter 12 to a detector (not shown) coupled to the proximal end of the catheter 12. The number of collection fibers 48 and illumination fibers 30 can range from one to one-hundred or more. Both the collection fibers 48 and the illumination fibers 30 can be arranged, for example, as one or more ring array(s). Alternatively, both the collection fibers 48 and the illumination fibers 30 can be arranged as rectilinear arrays or one or more half-ring array(s).

Each fiber, whether the fiber is a collection fiber 48 or an illumination fiber 30, has a core, a cladding having a lower index of refraction than the core, and a protective layer. However, one or more illumination or collection fibers 48 can include just a core and a protective layer, with no cladding. In one embodiment, the core and cladding are fused silica or glass, or fluorite glass. These materials are selected for their suitability in transmitting infrared radiation.

The re-entrant radiation is collected from a second annular region 52 by a second optical-redirector, which in this case is a collecting reflector 54, mounted in a proximal chamber 56 of the housing 26. The collecting reflector 54 is a frusto-conical structure having a narrow end 60 facing the input faces 58a–b of the collection fibers 48a–b and a flared end 62 facing the proximal surface 44 of the illuminating reflector 32. The proximal chamber 56 is a chamber having transparent walls, typically made of the same material as the housing. To avoid Fresnel reflections, the walls of the proximal chamber 56 are coated with an anti-reflective coating.

The flare angles of the illuminating reflector 32 and the collecting reflector 54 are typically on the order of 90 degrees and 45 degrees respectively. However, the flare angles are not limited to these values or ranges of values and can be selected to suit specific applications.

In operation, radiation incident onto a proximal surface 64 of the collecting reflector 54 is directed into the input faces 58a–b of the collection fibers 48a–b. The collection fibers 48a–b guide this radiation to a detector (not shown) coupled to the proximal end of the catheter 12. This radiation incident on a proximal surface 64 comes from the second annular region 52 on the inner wall 18. The location of the second annular region 52 depends on a flare angle of the collecting reflector 54.

In an additional mode of operation, the collection fibers 48a–b can also be coupled to a radiation source. In this case, the collecting reflector 54 functions as an additional illuminating reflector 32. In this mode, the apparatus functions as a light diffuser for spreading light to selected portions of the inner wall 18. This mode of operation might be used when, for example, a photochemical reaction is desired at a specific location or when pathologic tissue is to be ablated from a specific region.

The distance between the first and second annular regions 46, 52 enables the collecting reflector 54 to avoid collecting excessive specular reflection that would otherwise obscure the re-entrant radiation. The distance between the first and second annular regions 46, 52 depends on the flare angles of the collecting reflector 54 and the illuminating reflector 32, as well as the distance between the collecting reflector 54 and the illuminating reflector 32.

Figure 2:
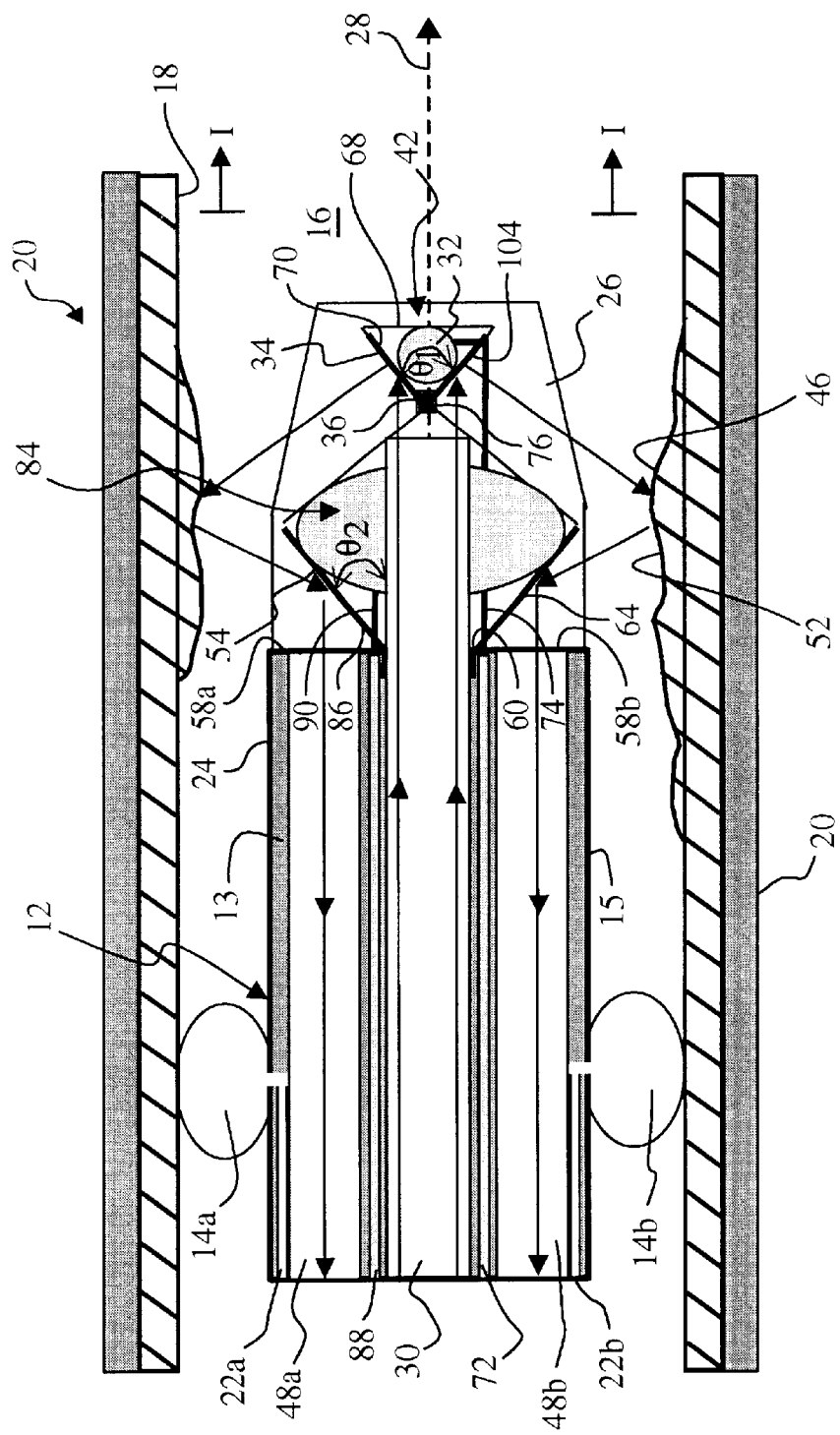
FIG. 2 is a longitudinal cross-section of a catheter with reflectors having variable flare angles controlled by balloons.

In the longitudinal cross-section of FIG. 1, the flare angles of the collecting and illuminating reflectors 32, 54 are fixed. However, in the embodiment shown in FIG. 2, the flare angle of the illuminating reflector 32 is adjusted by inflating or deflating a spherical balloon 68 coupled to a distal surface 70 of the illuminating reflector 32. The spherical balloon 68 is coupled to a first control fluid source at the proximal end of the catheter 12 (not shown) by a third control-fluid lumen 72 extending along the catheter 12 parallel to the longitudinal axis 28. At the distal tip 24 of the catheter 12, the third control-fluid lumen 72 connects to a first control-fluid pipe 74 that extends from the distal tip 24 of the catheter 12 to the spherical balloon 68.

The spherical balloon 68 is typically made of rubber, silicone rubber, fluorocarbon polymer, or soft plastic. The surface of the balloon 68 is covered with an anti-reflective coating to reduce stray Fresnel reflections.

In operation, when control fluid is added to the spherical balloon 68, the balloon 68 inflates. The inflating balloon 68 generates a force at the points of tangency of the illuminating reflector 32 with the balloon 68. This force causes the illuminating reflector 32 to dilate, thereby increasing the flare angle. When control fluid is withdrawn from the spherical balloon 68, the balloon 68 deflates. This causes the illuminating reflector 32 to contract, thereby reducing the flare angle.

In one embodiment, the balloon 68 is fixed to the distal surface 70 of the illuminating reflector 32 by an adhesive. As a result, deflation of the balloon 68 tends to pull the illuminating reflector 32 inward, toward the longitudinal axis 28. In another embodiment, the narrow end 36 of the illuminating reflector 32 is flexurally hinged to a support structure 76. In this case, the restoring force associated with the flexural hinge pulls the illuminating reflector 32 inward, toward the longitudinal axis 28.

Figure 3:
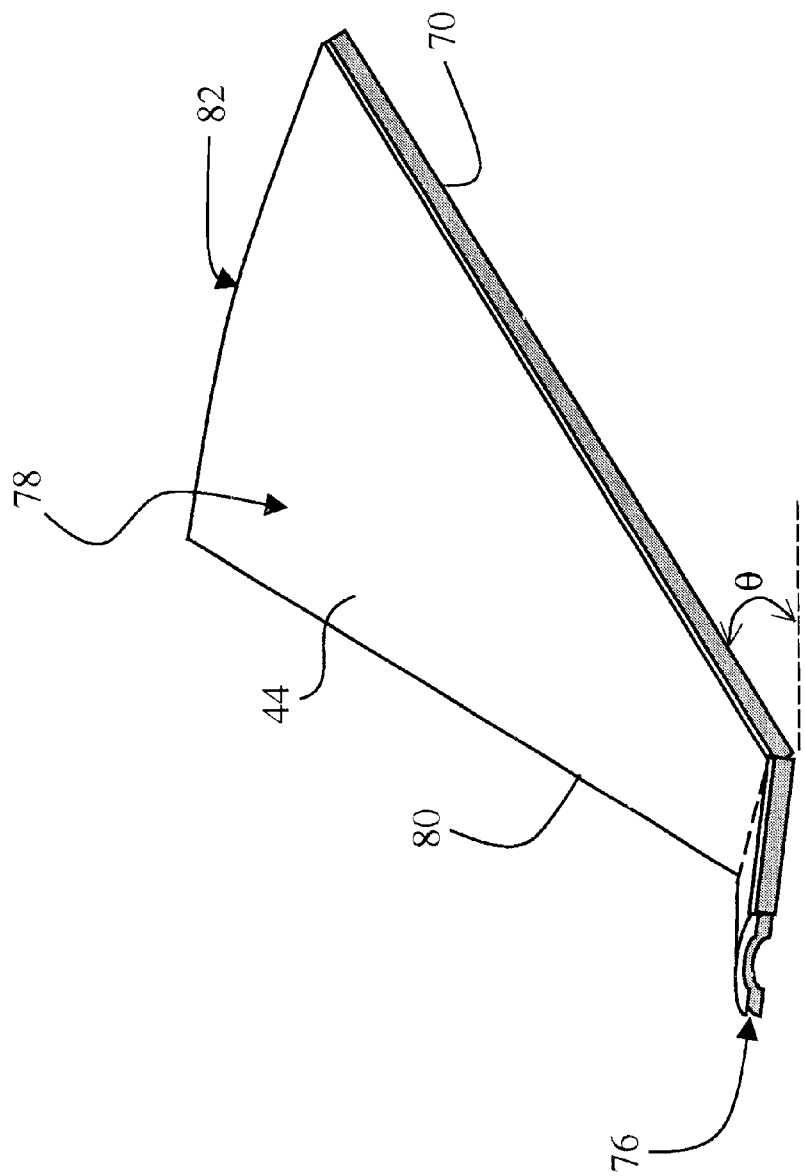
FIG. 3 is a schematic diagram of a reflecting panel from a reflector of the type shown in FIG. 2.

An illuminating reflector 32 that can dilate and contract in response to inflation and deflation of the spherical balloon 68 is made up of a plurality of fan-shaped panels 78 as shown in FIG. 3. Each panel 78 has a narrow end 80 and a wide end 82 distal to the narrow end 80. The narrow ends 80 of the panels 78 are circumferentially attached to the support structure 76. The width of the wide end 82 and the length of each panel 78 are selected so that adjacent panels 78 overlap each other, with the extent of the overlap being dependent on the volume of the balloon 68. When the balloon 68 is fully deflated, the extent of the overlap between adjacent panels 78 is at its greatest, and the flare angle is at its minimum. When the balloon 68 is fully inflated, the extent of the overlap between adjacent panels 78 is at its smallest, and the flare angle is at its maximum. The dimensions of the panel 78 are selected so that even when the flare angle is at its maximum, adjacent panels 78 continue to overlap with each other.

Reflecting panels 78 of the type shown in FIG. 3 are thus mechanically analogous to petals of a flower. The dilation and contraction of the illuminating reflector 32 as the overlap between panels 78 is changed is analogous to the manner in which a flower opens and closes as the overlap between adjacent petals increases or decreases.

The illuminating reflector 32 can have anywhere from one to thirty or more reflecting panels 78. The reflecting panels 78 are typically made of plastic, metal, or any other slightly elastic material. The proximal surface 44 of the panel 78 is coated with a reflective material such as nickel, silver, or gold. An anti-reflective coating on the distal surface 70 (i.e. the surface facing the spherical balloon) reduces stray Fresnel reflections.

Referring again to FIG. 2, the flare angle of the collecting reflector 54 is adjusted by inflating or deflating an annular balloon 84 coupled to a distal surface 86 of the collecting reflector 54. A fourth control-fluid lumen 88 extending along the catheter 12 parallel to the longitudinal axis 28 couples the annular balloon 84 to a second control fluid source at the proximal end of the catheter 12 (not shown). At the distal tip 24 of the catheter 12, the fourth control-fluid lumen 88 connects to a second control-fluid pipe 90 that extends from the distal tip 24 of the catheter 12 to the annular balloon 84.

In operation, when control fluid is added to the annular balloon 84, the balloon 84 inflates. The inflating annular balloon 84 generates a force at the points of tangency of the collecting reflector 54 with the balloon 84. This force causes the collecting reflector 54 to dilate, thereby increasing the flare angle. When control fluid is withdrawn from the annular balloon 84, the balloon 84 deflates. This causes the collecting reflector 54 to contract, thereby reducing the flare angle.

In one embodiment, the annular balloon 84 is fixed to the distal surface 86 of the collecting reflector 54 by an adhesive. As a result, deflation of the balloon 84 tends to pull the collecting reflector 54 inward, toward the longitudinal axis 28. In another embodiment, the narrow end 60 of the collecting reflector 54 is flexurally hinged to the illumination fiber 30. In this case, the restoring force associated with the flexural hinge pulls the collecting reflector 54 inward, toward the longitudinal axis 28.

An illuminating reflector 32 that can dilate and contract in response to inflation and deflation of the annular balloon 84 is made up of a plurality of fan-shaped panels 78 as already discussed above in connection with the spherical balloon 68.

Several dispositions of collection and illumination fibers 30, 48 are possible. In a first transverse cross-section, shown in FIG. 4, a ring of collection fibers 48a–f surrounds an illumination fiber 30 coaxial with the longitudinal axis 28 of the catheter 12. In a second transverse cross-section, shown in FIG. 5, a ring of illumination fibers 30a–h centered on the longitudinal axis 28 replaces the single illumination fiber 30 of FIG. 4. For clarity, only the central portion of the catheter 12 is shown in FIG. 5. The peripheral portion of the catheter 12, with its ring of collection fibers 48a–f, is identical to that shown in FIG. 4. In a third transverse cross-section, shown in FIG. 6, two concentric rings of collection fibers 48a–u replace the single ring of collection fibers 48a–f shown in FIG. 4.

Figure 7:
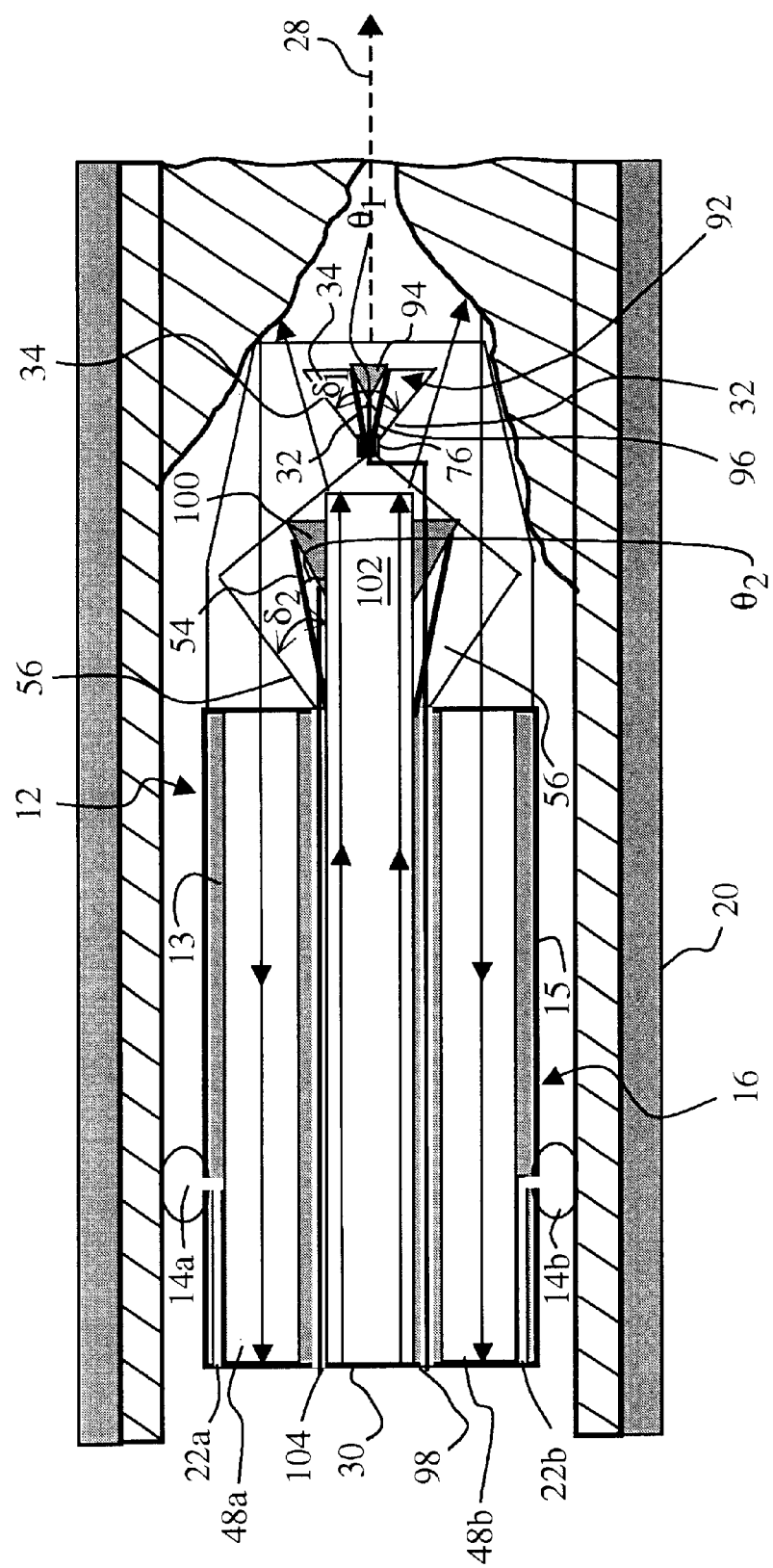
FIG. 7 is a longitudinal cross-section of a catheter with reflectors having variable flare angles controlled by translating cones.

The flare angle of the illuminating reflector 32 can also be adjusted by translating a first adjustment cone 92 along the longitudinal axis 28, as shown in longitudinal cross-section in FIG. 7. The first adjustment cone 92 has a base 94 and a vertex 96 proximal to the base 94. The first adjustment cone 92 is oriented so that its vertex 96 lies between its base 94 and the support structure 76 on which the illuminating reflector 32 is mounted. The first adjustment cone 92 is thus nested within the illuminating reflector 32 so that the illuminating reflector 32 and the first adjustment cone 92 intersect. The location of the intersection controls the flare angle of the illuminating reflector 32.

The first adjustment cone 92 is connected to a first control wire 98 that extends through the catheter 12. Pushing on the first control wire 98 causes the first adjustment cone 92 to translate distally along the longitudinal axis 28, thereby causing the flare angle of the illuminating reflector 32 to decrease. Conversely, pulling on the first control wire 98 causes the first adjustment cone 92 to translate proximally along the longitudinal axis 28, thereby causing the flare angle of the illuminating reflector 32 to increase.

It will be appreciated that an identical, or similar, mechanism for adjustment of flare angle can also be used for the collecting reflector 54. Such a mechanism is also shown in FIG. 7, in which a second adjustment cone 100 is nested inside the collecting reflector 54 in the same manner as the first adjustment cone 92 is nested inside the illuminating reflector 32. The principal difference between the first and second adjustment cone 92, 100 is that the second adjustment cone 100 has a central hole 102 to accommodate translation along the illumination fiber 30. The second adjustment cone 100 is likewise connected to a second control wire 104 that operates in the same manner as the first control wire 98.

Figure 4:
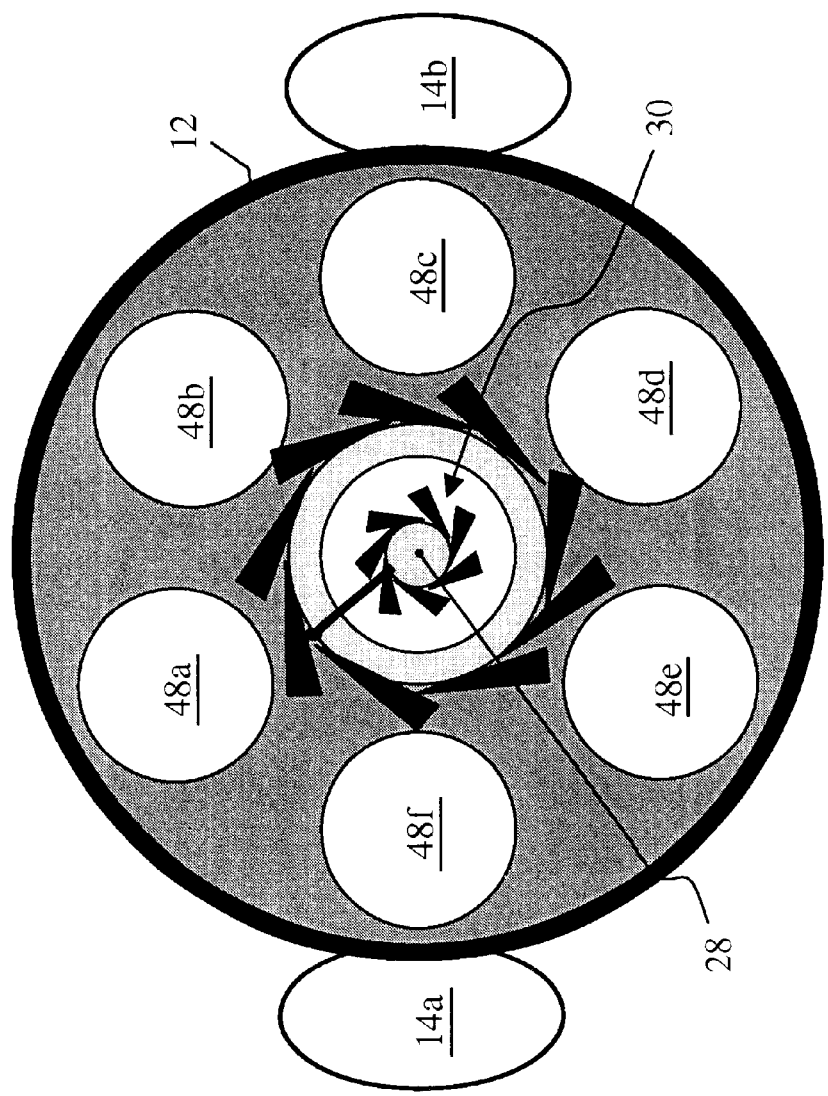
FIGS. 4–6 are transverse cross-sections of different arrangements of fibers in the catheter of FIG. 2.
Figure 5:
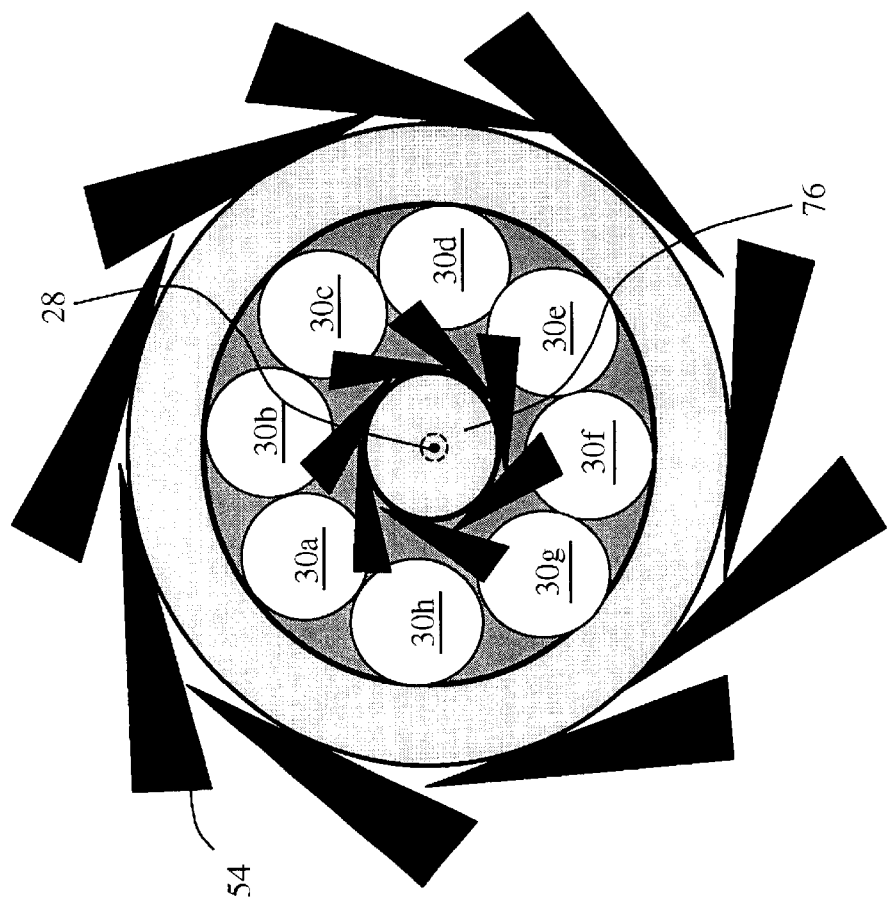
Figure 6:
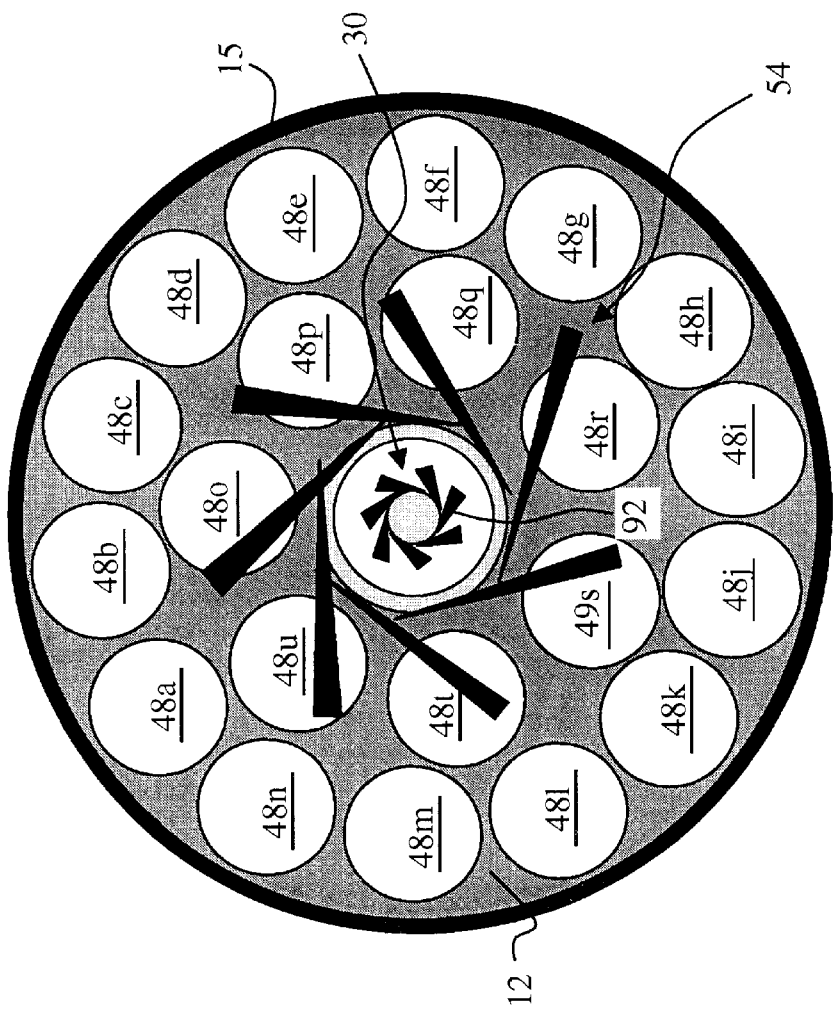
Figure 8:
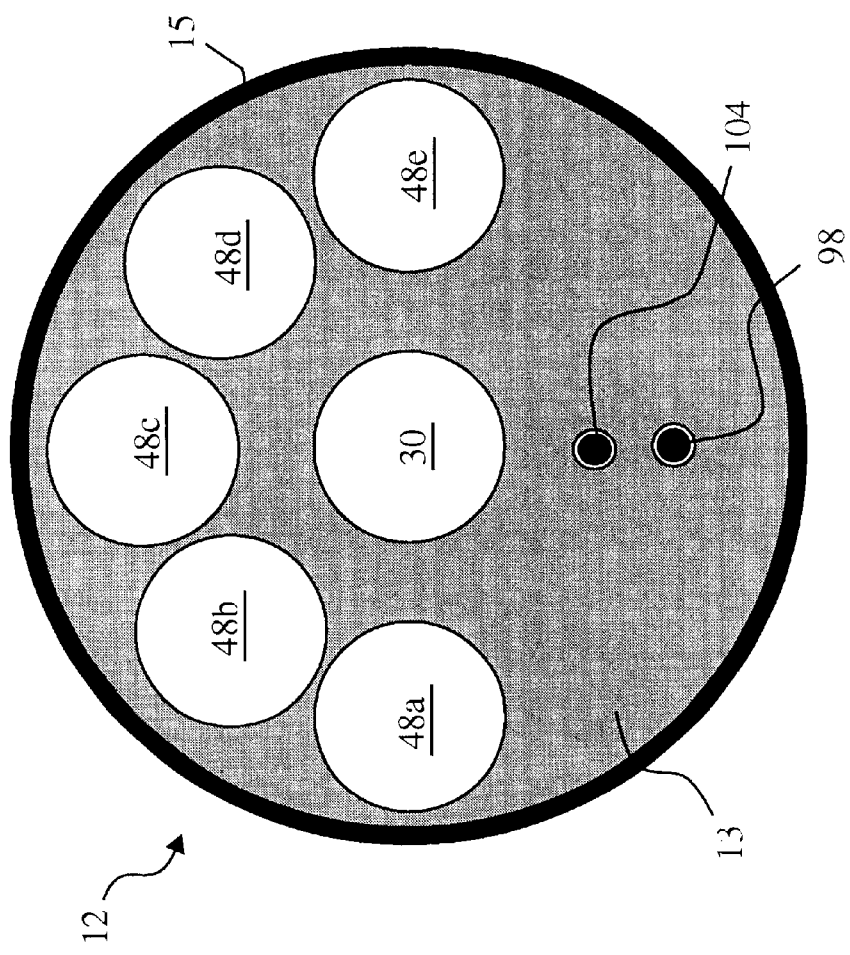
FIGS. 8 and 9 are transverse and longitudinal cross-sections of a catheter having a half-ring of collection fibers.
Figure 9:
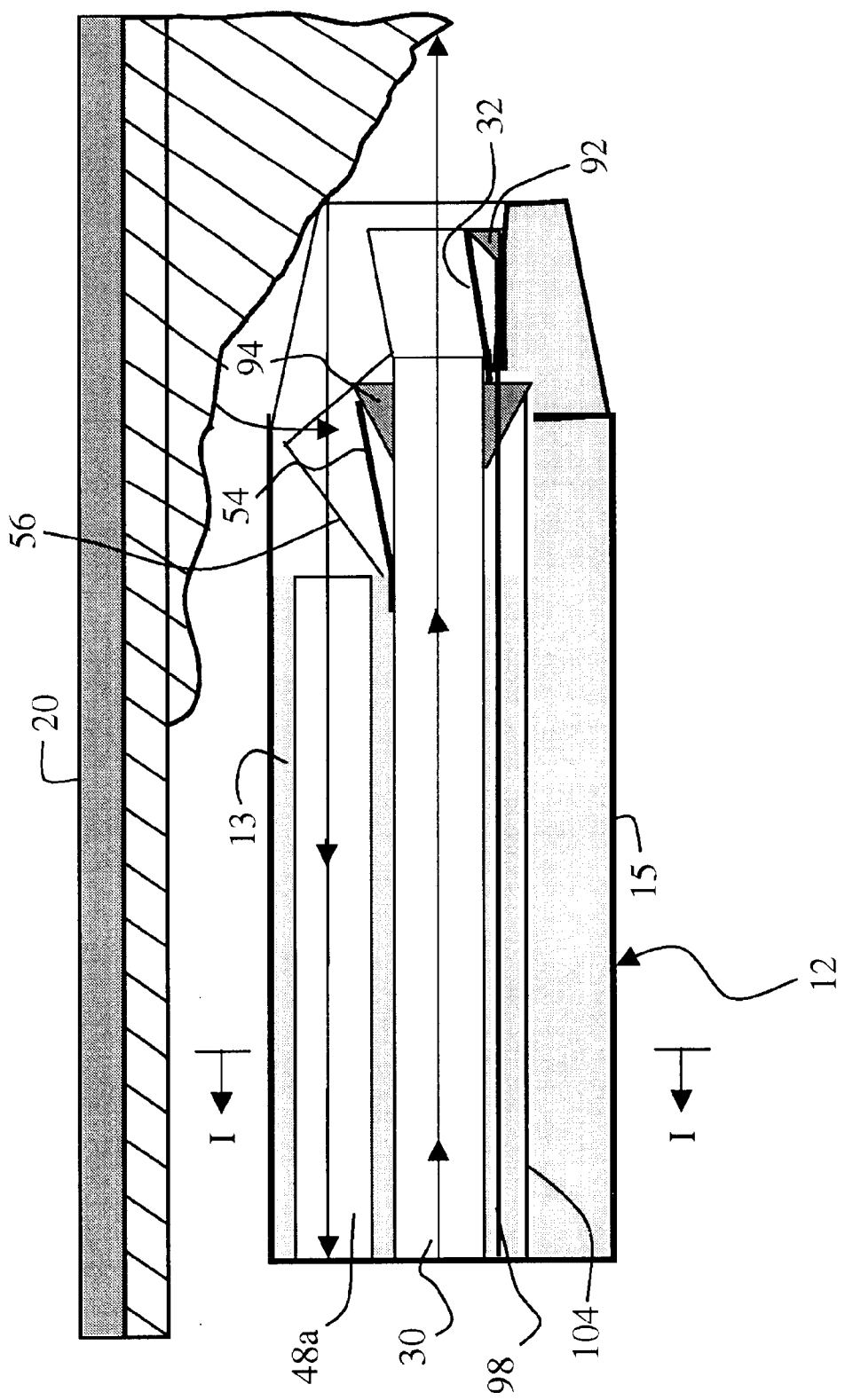

The collection fibers 48 need not be radially symmetric about the illumination fiber 30 as shown in the transverse cross-sections of FIGS. 4–6. For example, in the transverse cross-section of FIG. 8, the collection fibers 48a–e form a half-ring centered around the illumination fiber 30. This leaves more room for the first and second control wires 98, 104. From the corresponding longitudinal cross-section of FIG. 9, it is apparent that the illuminating reflector 32 can be a longitudinal slice of a cone and that the flare angle of the cone can be reduced so that the first region is no longer an annulus but a spot directly distal to the catheters tip.

Figure 10:
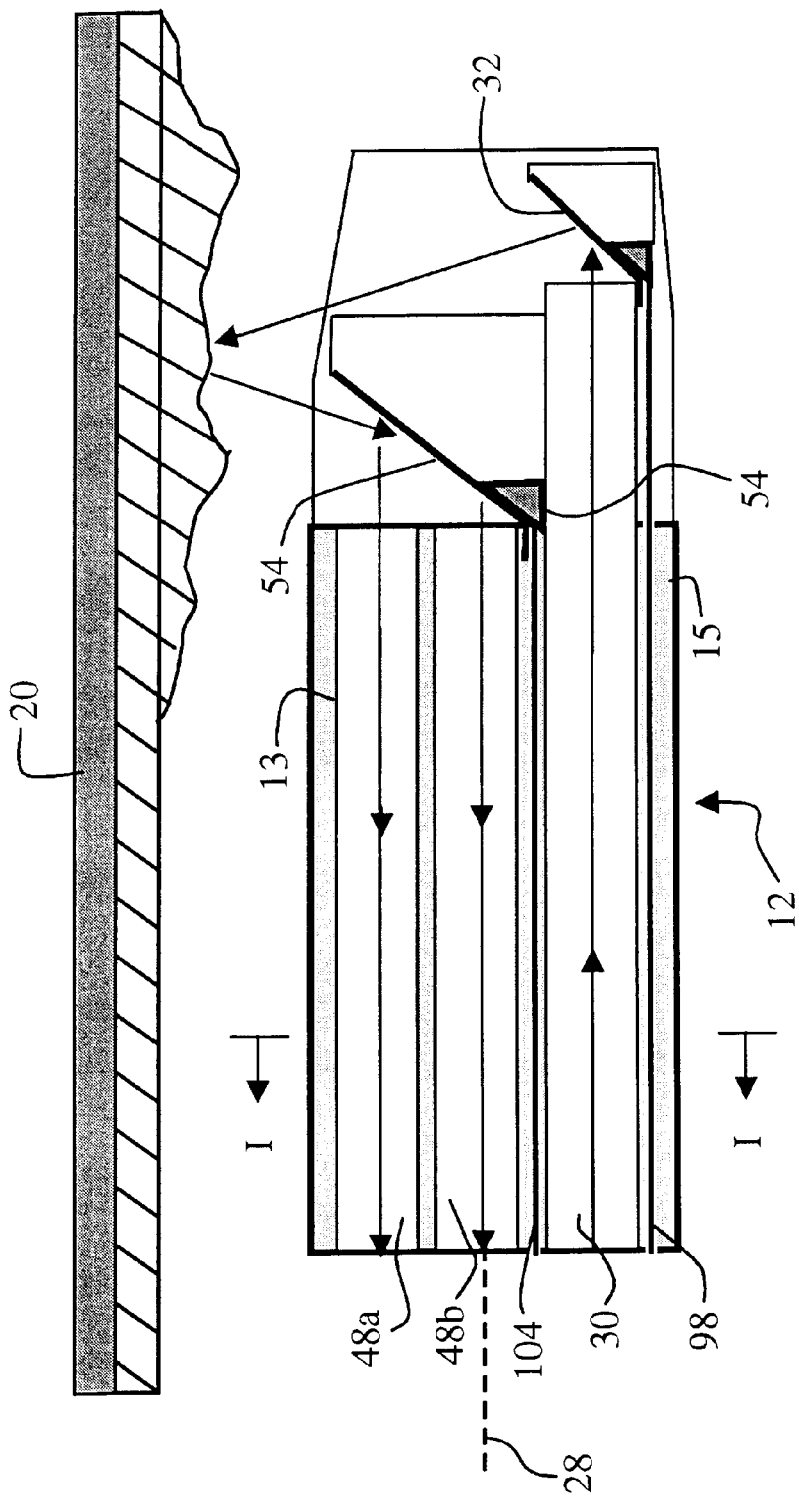
FIGS. 10 and 11 are longitudinal and transverse cross-sections of an embodiment in which the transmission fiber is disposed at the periphery of the catheter.
Figure 11:
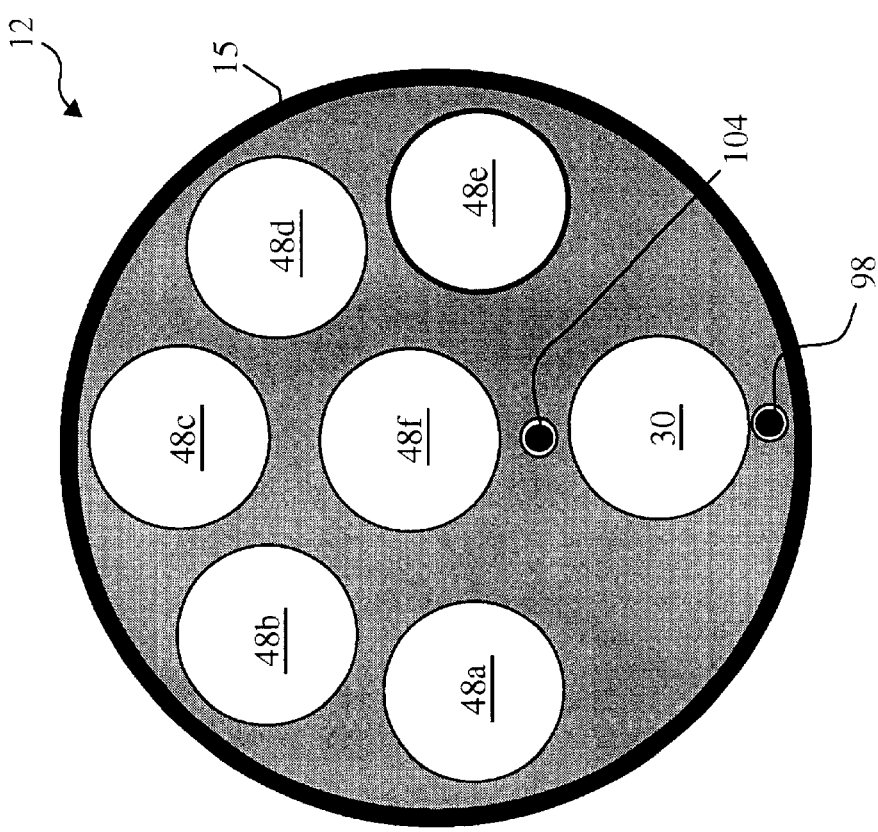

In the embodiments shown thus far, the illumination fiber 30 is centered within the catheter 12. However, this need not be the case. FIGS. 10 and 11 are longitudinal and transverse views of an embodiment in which the illumination fiber 30 is located at the periphery of the catheter 12 and a collection fiber 48b, rather than an illumination fiber 30, is collinear with the longitudinal axis 28.

As discussed above, the relative positions of the first and second regions 46, 52 on the inner wall 18 of the blood vessel 20 can be controlled by changing the flare angles of the illuminating reflector 32 and the collecting reflector 54, However, this is not the only method of controlling the relative positions. The relative positions between the first and second regions can also be changed by changing the position of the illuminating reflector 32 relative to that of the collecting reflector 54.

Figure 12:
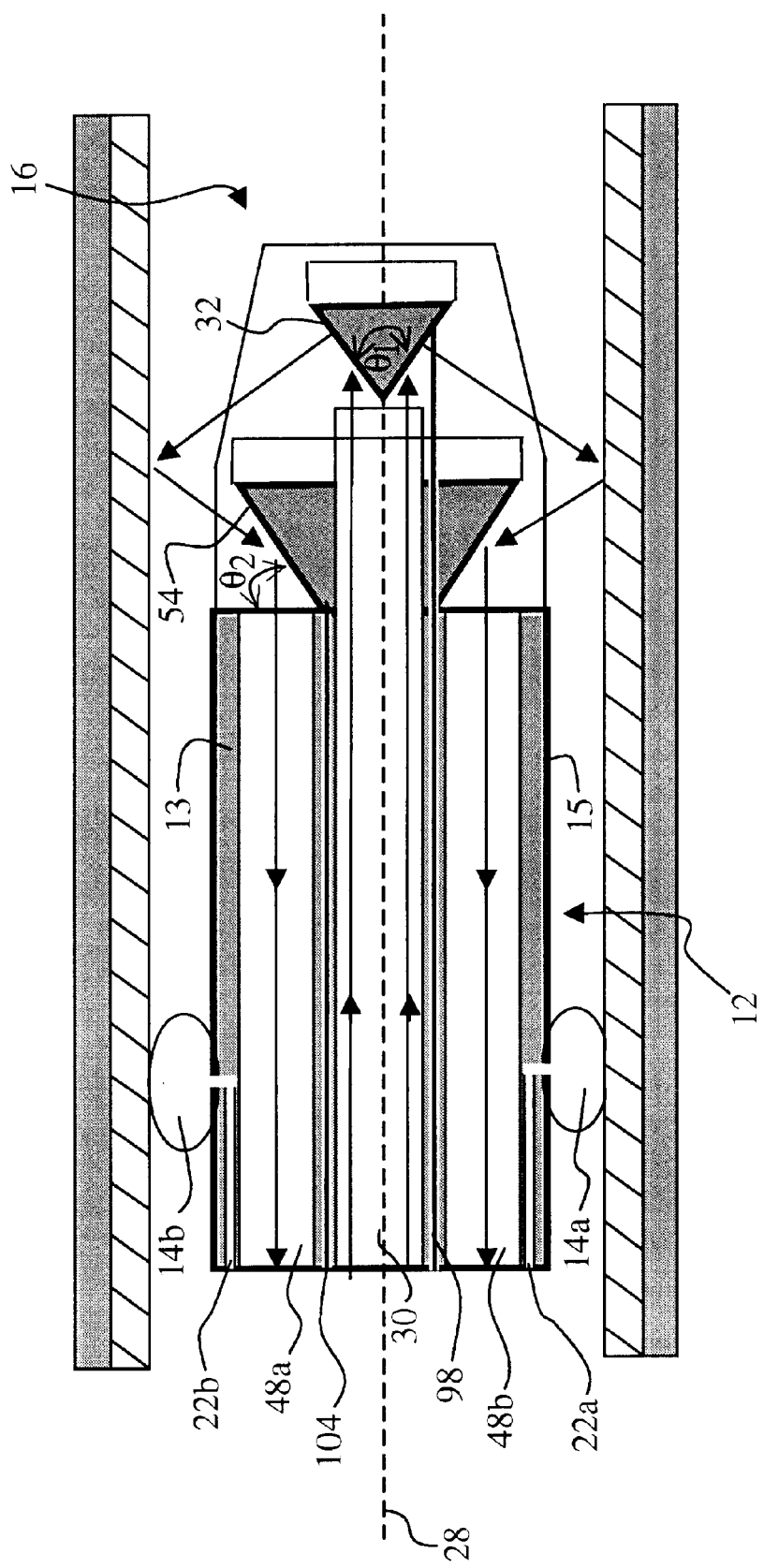
FIG. 12 is a longitudinal cross-section of a catheter in which the reflectors are translated relative to each other.

FIG. 12 shows an alternative embodiment in which the first and second control wires 98, 104 are connected directly to the illuminating reflector 32 and the collecting reflector 54 respectively. Pushing on the first control wire 98 causes the illuminating reflector 32 to translate distally along the longitudinal axis 28. Conversely, pulling on the first control wire 98 causes the illuminating reflector 32 to translate proximally along the longitudinal axis 28. Similarly, pushing and pulling on the second control wire 104 causes the collecting reflector 54 to translate proximally and distally along the longitudinal axis 28.

Figure 13:
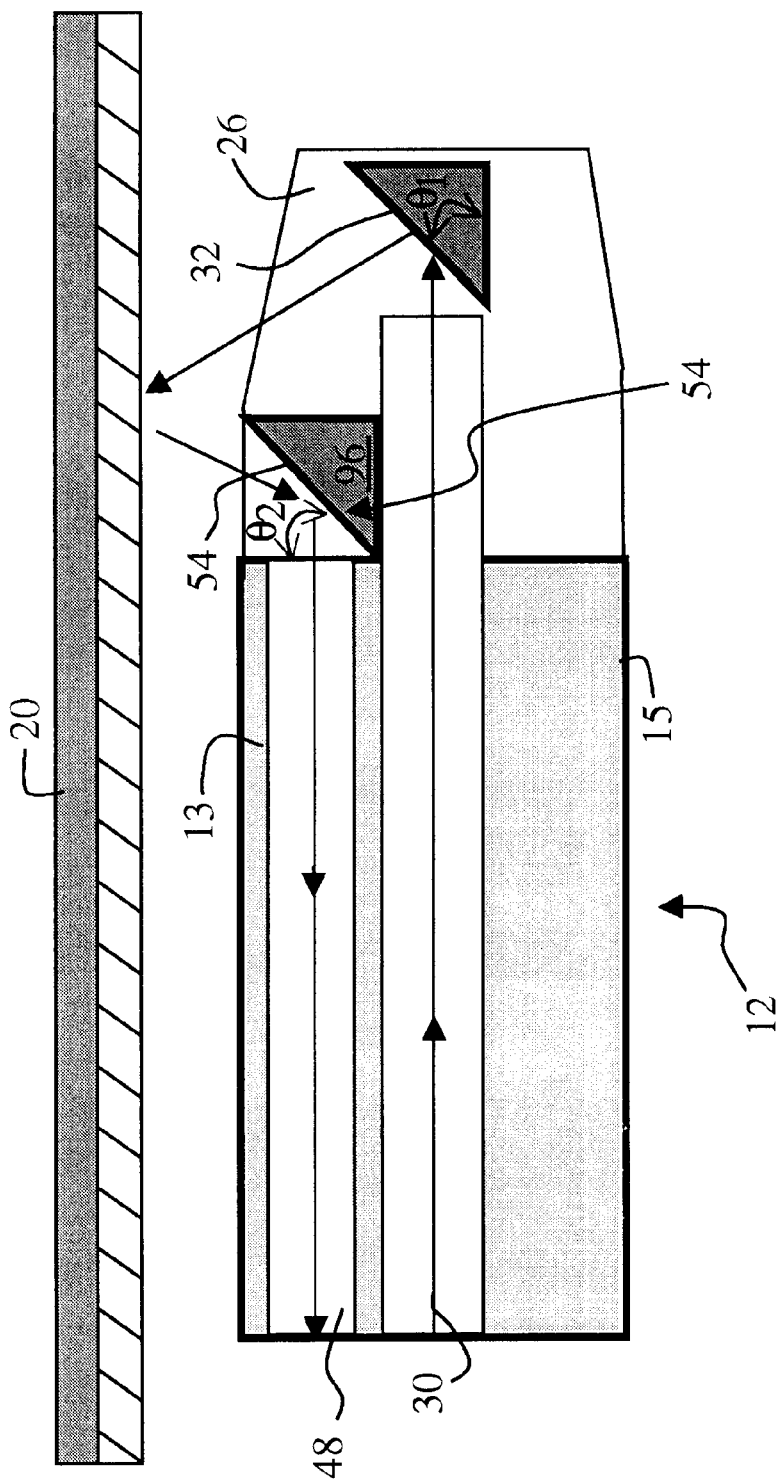
FIGS. 13 and 14 are longitudinal cross-sections of radially asymmetric versions of the catheters shown in FIGS. 1 and 12.
Figure 14:
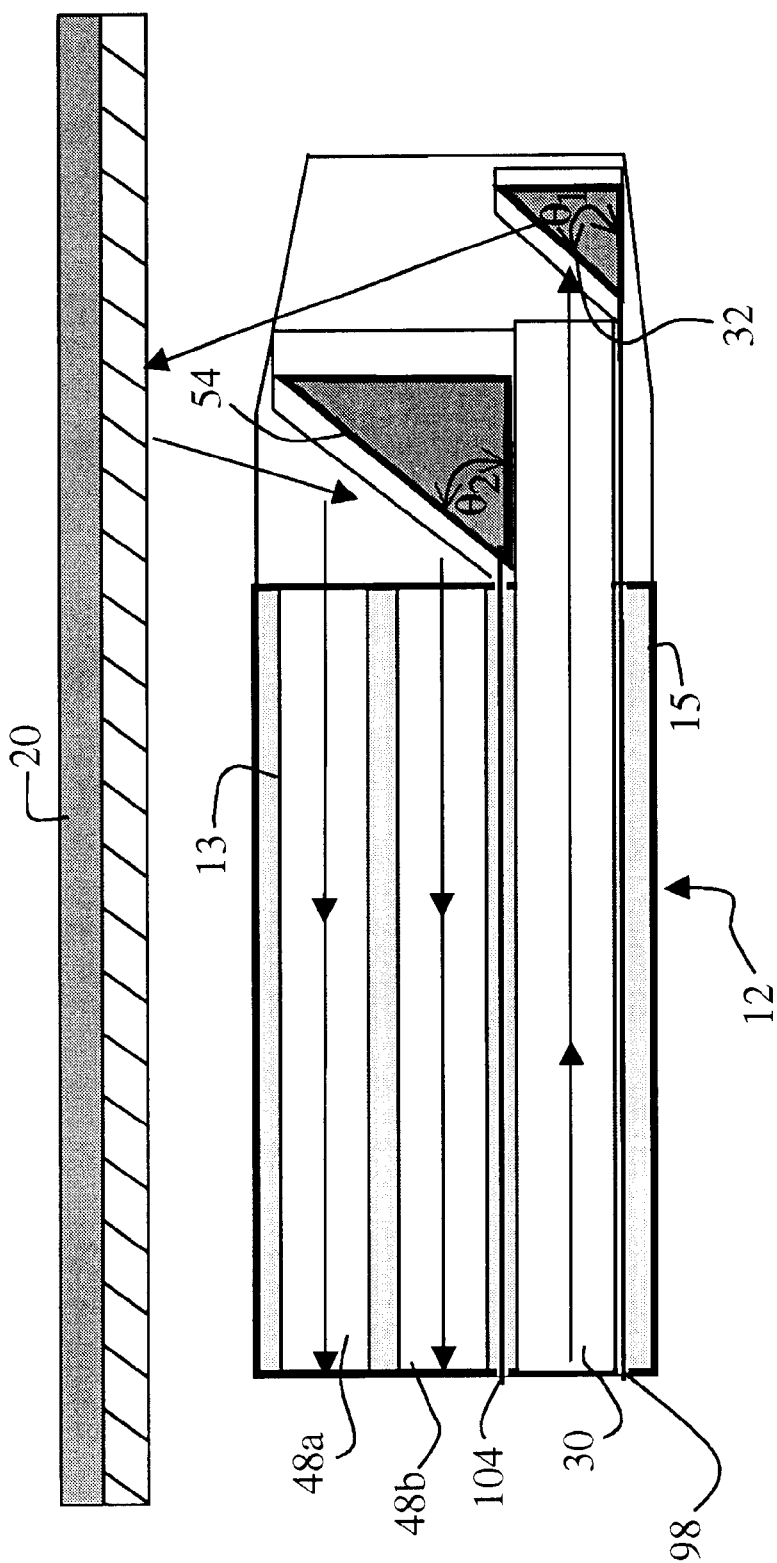

As noted in connection with FIGS. 10 and 11, the distribution of fibers and the placement of reflectors in a catheter 12 embodying the invention need not be radially symmetric. For example, in FIG. 10, the conical surfaces of the illumination and collection reflectors 32, 54 extend only halfway around the catheter 12. FIGS. 13 and 14 show analogous embodiments corresponding to the catheters 12 in FIGS. 1 and 12 respectively. Asymmetric embodiments such as these have a narrower circumferential field of view and can be for inspecting a limited portion of the inner walls circumference.

Figure 15:
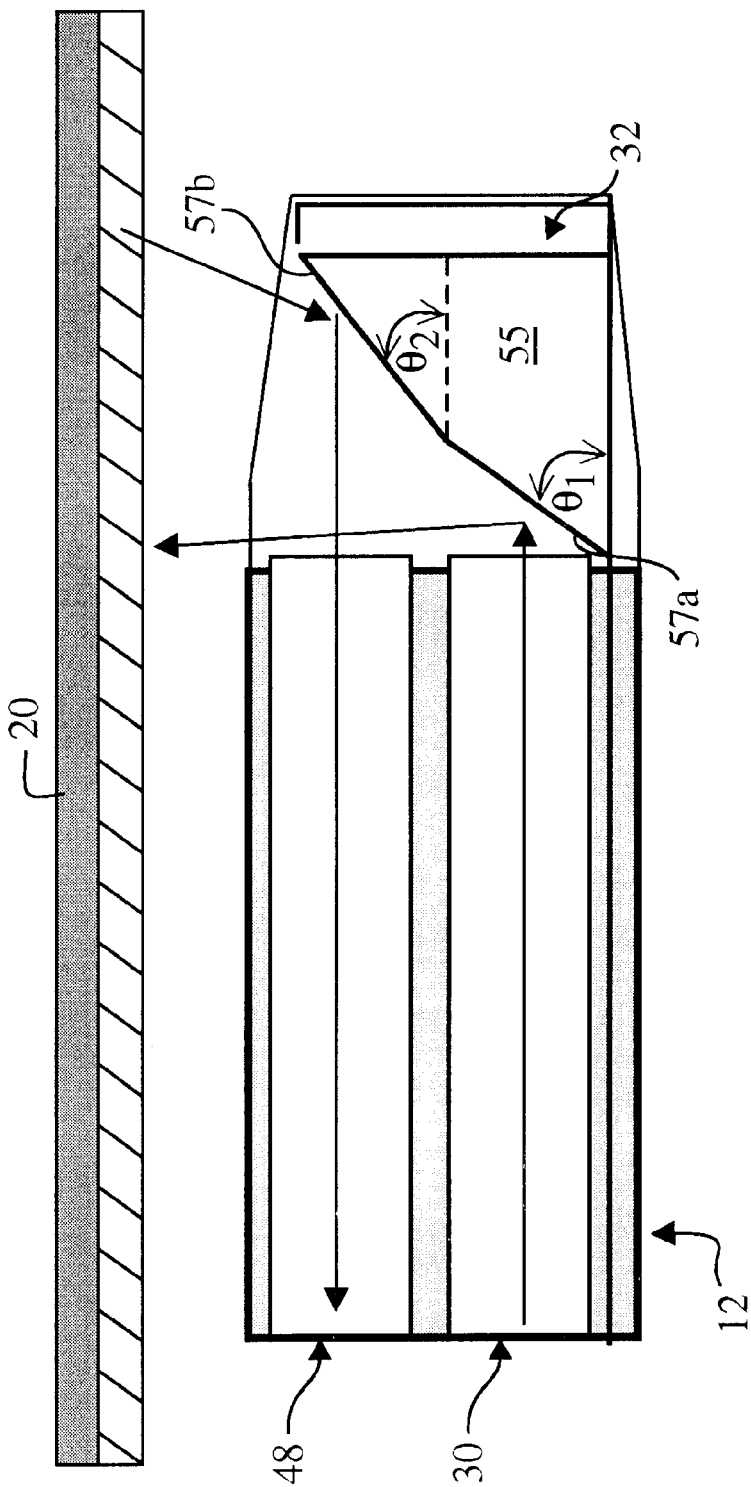
FIG. 15 is schematic diagram of an embodiment in which the reflectors are integrated into a single reflecting structure.

In the embodiments shown thus far, the illuminating reflector 32 and collecting reflector 54 are discrete structures. However, this need not be the case. For example, FIG. 15 shows a single reflecting member 55 having first and second facets 57a–b oriented at different angles. The first facet 57a forms the illuminating reflector 32 and the second facet 57b forms the collecting reflector 54. The illuminating and collecting reflectors 32, 54 are thus integrated into the same reflecting member 55.

Figure 16:
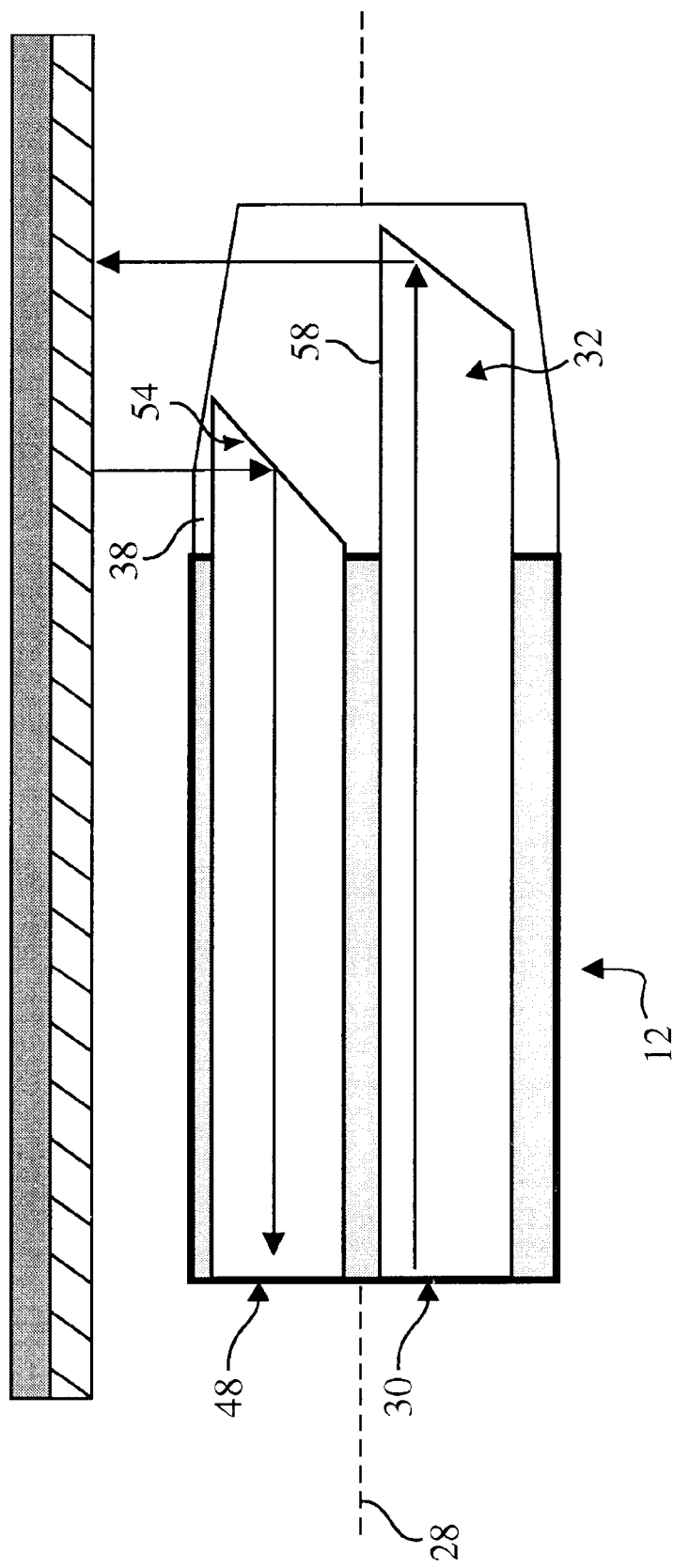
FIG. 16 is schematic diagram of an embodiment in which the reflectors are integrated into the waveguides.

The illuminating and collecting reflectors 32, 54 need not be formed on a separate reflecting element. For example, in the embodiment shown in FIG. 16, the input and output faces 38, 58 of the collection and illumination fibers 48, 30 face radially rather than the distally. As a result, the surface normal vectors of the input and output faces 38, 58 each have a radial component. This enables radiation traveling longitudinally on the fibers 48, 30 to be deflected toward the radial direction by an amount that depends on the angle of the surface normal vector relative to the longitudinal axis 28. In this embodiment, the illuminating reflector and the collecting reflector 32, 54 are integrated into the illumination and collection fibers 30, 48 themselves.

Figure 17:
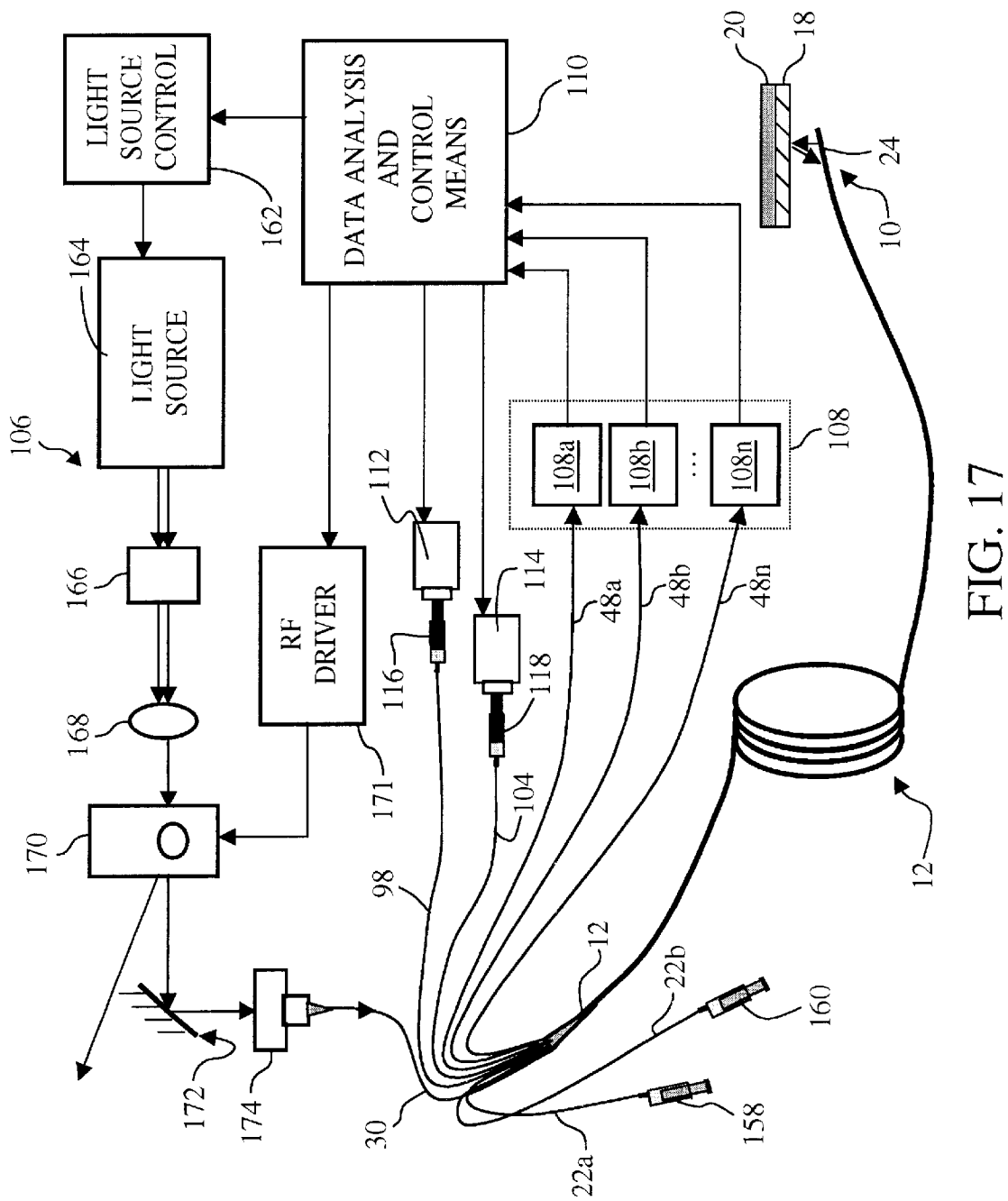
FIG. 17 is a schematic diagram showing a system that includes any one of the catheters described herein.

FIG. 17 shows any one of the previously described catheters 12 in use with other components of an optical measurement system 106. The following discussion of FIG. 17 refers to certain components that are not shown in the figure. These components, which are generally located in the distal portion 10 of the catheter 12, are shown in earlier figures, particularly FIG. 2. It is anticipated that one of ordinary skill in the art will have little difficulty in recognizing the relationship between the components shown in FIG. 17 and those shown in earlier figures.

The distal tip 24 of the catheter 12 is shown deployed adjacent to the inner wall 18 of a blood vessel 20. At the proximal end of the catheter 12, the collection fibers 48a–n are coupled to a set of detectors 108a–n, the outputs of which are connected to a processor 110. The processor 110 includes a pair of outputs coupled to first and second motors 112, 114 that drive corresponding first and second actuators 116, 118. The motors 112, 114 can be stepper motors, servomotors, or any other kind of motor.

The first and second actuators 116, 118 are coupled to either spherical or annular balloons 68, 84 or to control wires 98, 104 that control the positions and/or flare angles of the illuminating reflector 32 and the collecting reflector 54 respectively. The processor 110 thus completes a feedback loop in which the actuators 116, 118 are controlled on the basis of signals received from the collection fibers 48a–n.

FIG. 18 shows an actuator 116 for controlling inflation of a balloon 68, 84 when the control fluid is a gas. The actuator 116 includes a gas-filled cylinder 120 having a distal end 122 coupled to one of the third and fourth control-fluid lumens 72, 88, and a proximal end 124 for accommodating a piston 126 mounted at a distal end 128 of a shaft 130. As the motor 112, 114 translates the piston 126 within the cylinder, gas flows into or out of the control-fluid lumen 72, 88, thereby changing the size of the balloon 68, 84.

FIG. 19 shows an actuator 116 for controlling inflation of a balloon 68, 84 when the control fluid is a liquid. The actuator 116 includes a liquid-filled cylinder 132 having a distal end 134 coupled to one of the third and fourth control-fluid lumens 72, 88, and a proximal end 136 for accommodating a piston 138 mounted at a distal end 140 of a screw 142. As the motor 112, 114 turns the screw 142 clockwise or counter-clockwise, the piston 138 is translated within the cylinder 132 causing liquid to flow into or out of the control-fluid lumen 72, 88, thereby changing the size of the balloon 68, 84.

FIG. 20 shows an actuator 116 for controlling the position of the first and second adjustment cones 92, 100 or for translating the illuminating and collecting reflectors 32, 54 (shown in FIG. 7) directly. The actuator 116 includes a cylinder 144 having a proximal end 146 that accommodates a piston 148 mounted at a distal end 150 of a screw 152. A control wire 98, 104 fixed to the piston 148 extends distally, toward a distal end 154 of the cylinder 144. The control wire 98, 104 passes through the distal end 154 of the cylinder 144 and continues into the catheter 12. Seated between the distal end 154 of the cylinder 144 and the piston 148 is a spring 156 for providing a restoring force. As the motor 112, 114 turns the screw 152 clockwise or counter-clockwise, the piston 148 is translated within the cylinder 144. This causes a pulling or pushing of the control wire 98, 104 that in turn causes longitudinal movement of either an adjustment cone 92, 100 or one of the illuminating or collecting reflectors 32, 54 (shown in FIG. 2).

Third and fourth actuators 158, 160 of the type described in connection with FIGS. 18 and 19 are also coupled to the first and second control-fluid lumens 22*a–b* for controlling the positioning balloons 14*a–b*. In the embodiment shown in FIG. 17, the third and fourth actuators 158, 160 are manually controlled. However, the third and fourth actuators 158, 160 can also be driven by motors coupled to the processor 110 to form a feedback loop that centers the catheter 12 within the blood vessel 20.

As shown in FIG. 17, the processor 110 includes an output for providing a control signal to a radiation source controller 162. The radiation source controller 162 is coupled to a radiation source 164 that operates in response to instructions provided by the radiation source controller 162. The radiation source 164 can include one or more fixed frequency or tunable lasers. Alternatively, the radiation source can include one or more conventional lamps, one or more GaAlN or GaN based LEDs, reflectors(s), narrow band filter(s), and optical focusing element(s). The wavelength of radiation is in the ultraviolet range, visible range, or in the infrared range, including both the near and far infrared range. However, the scope of the invention is not restricted to specific wavelengths or frequency bands.

Radiation from the radiation source 164 passes through an isolator 166 to prevent radiation from being reflected back into the radiation source 164. Collimating lenses 168 coupled to an output of the isolator 166 then focus radiation into a modulator 170, where the radiation is mixed with an RF (radio frequency) signal provided by an RF source 171. A suitable frequency of modulation is in a range from approximately 25 kHz to 100 kHz. This modulation shifts the radiation up in frequency so that the processor 110 can more easily recover the re-entrant radiation from the background noise. The modulated radiation is then directed into the illumination fiber 30 by a mirror 172 and a fiber coupler 174.

Other Embodiments

It is to be understood that while the invention has been described in conjunction with the detailed description thereof, the foregoing description is intended to illustrate and not limit the scope of the invention.

For example, either the illuminating reflector, the collecting reflector, or both can be replaced by a refracting element that similarly causes a change in the direction of radiation. A refracting element, such as a prism, could steer the radiation by physical rotation or translation of the prism, using actuators as described herein, In addition, it is known that the permittivity, and hence the index of refraction, of certain materials (e.g., nematic liquid crystals) can be altered by application of electric or magnetic fields. An alternative embodiment with no moving parts could therefore be manufactured by constructing the prism of such a material and selectively changing the prisms index of refraction by suitable exploitation of such electro-optic and magneto-optic effects.

The invention is defined by the scope of the appended claims. Other aspects, advantages, and modifications are within the scope of the following claims.

We claim:

1. An apparatus comprising:
   a conduit having a longitudinal axis extending between a proximal portion and a distal portion;
   a first waveguide for guiding radiation between the proximal portion of the conduit and the distal portion of the conduit;
   a second waveguide for guiding radiation between the proximal portion of the conduit and the distal portion of the conduit;
   a first optical-redirector disposed on an optical path between the first waveguide and a target, the first optical-redirector being oriented to direct radiation along a first path extending between the first waveguide and the target; and
   a second optical-redirector disposed on an optical path between the second waveguide and the target, the second optical-redirector being oriented to direct radiation along a second path extending between the second waveguide and the target.

2. The apparatus of claim 1, wherein the first optical-redirector comprises a conical surface having a cone axis parallel to the longitudinal axis of the conduit, the conical surface having a flare angle relative to the cone axis.

3. The apparatus of claim 2, wherein the conical surface comprises a truncated half-cone.

4. The apparatus of claim 2, wherein the conical surface comprises a truncated cone.

5. The apparatus of claim 2, further comprising an actuator coupled to the conical surface for adjusting the direction of the first path.

6. The apparatus of claim 5, wherein the actuator is configured to change the flare angle of the conical surface.

7. The apparatus of claim 5, wherein the actuator is configured to translate the conical surface along the longitudinal axis.

8. The apparatus of claim 5, wherein the actuator comprises an inflatable balloon coupled to the conical surface so that a change in a volume of the balloon controls the flare angle.

9. The apparatus of claim 5, wherein the actuator comprises a translating member coupled to the conical surface so that translation of the translating member controls the flare angle.

10. The apparatus of claim 5, wherein the actuator comprises a control wire coupled to the conical surface for translating the conical surface along the longitudinal axis.

11. The apparatus of claim 5, wherein the conical surface comprises a plurality of reflecting panels, each of the reflecting panels having a base end and a free end longer than the base end, each reflecting panel being pivotable about the base end between a closed position and an open position.

12. The apparatus of claim 11, wherein adjacent reflecting panels overlap such that when each reflecting panel is pivoted to its open position, the plurality of reflecting panels forms a continuous reflecting surface.

13. The apparatus of claim 1, wherein the first and second optical-redirectors are stationary relative to each other.

14. The apparatus of claim 1, further comprising a first actuator coupled to the first optical-redirector for moving the first optical-redirector relative to the second optical-redirector.

15. The apparatus of claim 14, further comprising a feedback loop for moving the first optical-redirector relative to the second optical-redirector on the basis of a signal received from at least one of the first optical-redirector or the second optical-redirector.

16. The apparatus of claim 15, wherein the feedback loop comprises:
a detector in communication with the second waveguide;
a motor in communication with the first actuator; and
a processor in communication with the detector and with the motor, the processor being configured to drive the motor in response to a signal received from the detector.

17. The apparatus of claim 1, wherein the first optical-redirector comprises a reflecting surface.

18. The apparatus of claim 1, wherein the first optical-redirector comprises a refracting element.

19. The apparatus of claim 1, wherein the first optical-redirector comprises a first reflecting facet of a reflecting member and the second optical-redirector comprises a second reflecting facet of the reflecting member.

20. The apparatus of claim 1, wherein the first optical-redirector is integrated into the first waveguide.

21. The apparatus of claim 20, wherein the first waveguide includes a distal face having a surface normal vector with a radial component for directing radiation along a first path extending between the distal face and the target.

22. The apparatus of claim 1, wherein the first optical-redirector is adapted to direct infrared radiation along the first path.

23. The apparatus of claim 1, wherein the conduit has a diameter between approximately 1 millimeter and 15 millimeters.

24. The apparatus of claim 1, wherein the conduit comprises a catheter.

25. An apparatus comprising:
a first optical-redirector mounted on a distal end of a catheter for coupling radiation to a target along a first path extending between the first optical-redirector and the target;
a second optical-redirector mounted on the distal end of the catheter for coupling radiation to a target along a second path extending between the second optical-redirector and the target.

26. The apparatus of claim 25, further comprising a first steering mechanism coupled to the first optical-redirector for selecting the first path.

27. The apparatus of claim 26, further comprising a second steering mechanism coupled to the second optical-redirector for selecting the second path.

28. A method comprising:
directing illuminating radiation along a first path extending between the catheter and the target, the first path having a radial component orthogonal to a longitudinal axis of the catheter; and
collecting re-entrant radiation from the target along a second path extending between the target and the catheter, the second path having a radial component orthogonal to a longitudinal axis of the catheter.

29. The method of claim 28, further comprising analyzing the re-entrant radiation to detect a structure on or in the target.

30. The method of claim 28, further comprising selecting the first path and/or the second path to enhance recovery of the re-entrant radiation.

* * * * *